(12) United States Patent
Drent et al.

(10) Patent No.: US 7,098,369 B2
(45) Date of Patent: Aug. 29, 2006

(54) PROCESS FOR THE PRODUCTION OF PRIMARY ALCOHOLS

(75) Inventors: Eit Drent, Amsterdam (NL); Renata Helena Van Der Made, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/669,916

(22) Filed: Sep. 24, 2003

(65) Prior Publication Data
US 2004/0133050 A1 Jul. 8, 2004

(30) Foreign Application Priority Data
Sep. 26, 2002 (EP) ............................................ 02256698

(51) Int. Cl.
*C07C 29/145* (2006.01)
*C07C 29/16* (2006.01)

(52) U.S. Cl. ........................ 568/881; 568/885; 568/903; 568/876; 568/878; 568/880; 568/884; 568/902

(58) Field of Classification Search ................. 568/881, 568/885, 903, 876, 878, 880, 884, 902
See application file for complete search history.

(56) References Cited

U.S. PATENT DOCUMENTS

| | | | |
|---|---|---|---|
| 2,042,011 A | 5/1936 | Loomis ........................ | 166/21 |
| 5,780,684 A | 7/1998 | Drent et al. | |
| 5,994,591 A | 11/1999 | Arnoldy et al. .............. | 568/454 |
| 6,037,500 A | 3/2000 | Zhang .......................... | 568/12 |
| 6,103,927 A | 8/2000 | De Castro Loureiro Barreto Rosa et al. ..... | 560/207 |
| 6,156,936 A | 12/2000 | Drent et al. ................. | 568/454 |
| 6,290,926 B1 | 9/2001 | Haenel et al. ............ | 423/437.2 |

FOREIGN PATENT DOCUMENTS

| | | |
|---|---|---|
| DE | 101 06 348 A1 | 2/2001 |
| EP | 0 499 329 B1 | 5/1994 |
| EP | 0900776 A1 | 8/1998 |
| EP | 0922691 A1 | 6/1999 |
| EP | 0971940 B1 | 6/2002 |
| FR | 2671132 | 7/1992 |
| GB | 2306344 | 5/1997 |
| WO | WO 95/05354 | 2/1995 |
| WO | WO 95/06027 | 3/1995 |
| WO | WO 95/3680 | 11/1995 |
| WO | 95/30680 | 11/1995 |
| WO | WO 98/42717 | 10/1998 |
| WO | WO 00/56695 | 9/2000 |
| WO | 01/14299 A1 | 3/2001 |
| WO | WO 01/28972 A1 | 4/2001 |
| WO | WO 01/87899 A1 | 11/2001 |
| WO | WO 02/14248 A2 | 2/2002 |
| WO | 02/26690 A1 | 4/2002 |
| WO | 02/36261 A2 | 5/2002 |
| WO | 02/057278 A1 | 7/2002 |
| WO | WO 02/064250 A2 | 8/2002 |
| WO | WO 03/040065 A2 | 5/2003 |

OTHER PUBLICATIONS

U.S. Appl. No. 10/287,731, filed Nov. 4, 2002, Drent et al.
Elsner et al., Chemical Abstract 1978, vol. 89, 180154x.
U.S. Appl. No. 10/670,105, filed Sep. 24, 2003, Drent. et al.
International Search Report of Feb. 23, 2004.
"Hydroformylation of Internal Olefins to Linear Aldehydes with Novel Rhodium Catalysts," by L.A. van der Veen, P. C. J. Kamer, and P. W. N. M. van Leeuwen, *Angew Chem. Int. Ed.* 1999, 8, No. 3, XP–000960496, pp. 336–338.
"On the mechanism of the thermal tetramerization of phospholes," by M. O. Bevierre, F. Mercier, L. R. F. Mathey, *Bull. Soc. Chem. Fr.* (1992) 129, XP–002083579.
"Versatile Ligands for Palladium–Catalyzed Asymmetric Allylic Alkylation," by P. Dierkes et al., *Angew Chem. Int. Ed.* 1998, 37, No. 22, XP–002195282, pp. 3116–3118.
"Palladium–catalyzed enantioselective multiple carbonylation of 1–olefins. Synthesis of optically active 2–oxo–pentanedioates and butanedioates," by Martin Sperrle, Giambattista, Consiglio, *Inorganica Chimica Acta* 300–302 (2000) XP–002281244, pp. 264–272.
"Combining the Chemistry of Phospholes and Phosphinines," bu K. Waschbuesch, P. Le Floch, F. Mathey, *Inorfanica Chimica Acta* 300–302 (2000) XP–002281245, pp. 270–272.
"Asymmetric Reactions Catalyzed by Chiral Metal Complexes. LXXXV. Synthesis of New Atropisomeric Bisphosphine Ligands Bearing Chiral Phospholane and Their Use in Assymetric Hydrogenation," by N. Fujie, M. Matsui, K. Achiwa, *Chemical & Pharmaceutical Bulletin* (1999), 47(3), XP–002281246, pp. 436–439.
"Diene Derivatives of Phospholenes as Monomers for Obtaining Sorption Active Polymers," by B. A. Arbuzovet al., DE 101 06 348 A1, XP–002281247.

*Primary Examiner*—Elvis Price
(74) *Attorney, Agent, or Firm*—Donald F. Haas

(57) ABSTRACT

A process for producing primary alcohols from secondary alcohols and/or tertiary alcohols and/or ketones, wherein the process comprises reacting a compound selected from a secondary alcohol, a tertiary alcohol, a ketone, or mixtures thereof, with carbon monoxide and hydrogen in the presence of a catalyst based on:
(i) a source of Group VIII metal,
(ii) a bidentate ligand having the general formula (I):

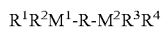

$$R^1R^2M^1\text{-}R\text{-}M^2R^3R^4 \qquad (I)$$

wherein $M^1$ and $M^2$ are independently P, As or Sb;
  $R^1$ and $R^2$ together represent a bivalent substituted or unsubstituted cyclic aliphatic group whereby the two free valencies are linked to $M^1$; $R^3$ and $R^4$ independently represent a substituted or unsubstituted hydrocarbyl group, or together represent a bivalent or non-substituted cyclic group whereby the two free valencies are linked to $M^2$; and
R represents a bivalent aliphatic bridging group; and
(iii) an acid having a $pK_a$ of 3 or less which is in excess over the Group VIII metal.

24 Claims, No Drawings

PROCESS FOR THE PRODUCTION OF PRIMARY ALCOHOLS

FIELD OF THE INVENTION

The present invention relates to a process for producing primary alcohols. In particular, the present invention relates to a process for producing primary alcohols from secondary and/or tertiary alcohols and/or ketones.

BACKGROUND OF THE INVENTION

Higher primary alcohols, such as those in the $C_{10}$–$C_{18}$ range, are well known and useful compounds which are suitable for a wide variety of products and applications. For example, they can be usefully converted to surfactants by sulphation and/or ethoxylation and used in laundry detergents and other household cleaning products.

Methods for producing primary alcohols are well known in the art. Unfortunately, it is not commercially viable to produce primary alcohols directly from the oxidation of paraffins. This is because the oxidation of paraffins produces primarily secondary alcohols, tertiary alcohols or ketones, or a mixture of these compounds, but does not produce high yields of primary alcohols. Therefore, despite paraffins being a relatively inexpensive feedstock, it is necessary to use other methods of producing primary alcohols.

One well known and commercially used method for producing primary alcohols is the hydroformylation of olefins using a homogeneous hydroformylation catalyst. Using such a method, primary alcohols of high selectivity and yield can be produced. For such methods it is necessary to use an olefin feed as starting material. Olefins can be produced by various methods including the oligomerisation of ethylene.

WO 95/05354 describes the hydroformylation of ethylenically unsaturated compounds by reaction with carbon monoxide and hydrogen in the presence of a catalyst system comprising a Group VIII metal cation, viz. cationic palladium, and a bidentate ligand, viz. a diphosphine. In the examples several bidentate diphosphines are used.

However, currently known methods for producing primary alcohols suffer from the disadvantage that they are restricted to feedstock which is relatively expensive, notably ethylene, which is produced via the thermal cracking of paraffins. In addition, current methods require several steps, and several catalyst types. Considering the production of primary alcohols by hydroformylation, first it is necessary to prepare ethylene via the thermal cracking of paraffins. Thereafter it is necessary to prepare an olefin feed, for example by ethylene oligomerization in the presence of an oligomerization catalyst, and finally, in a further separate step, the olefins are converted to alcohols by hydroformylation in the presence of a hydroformylation catalyst.

From the viewpoint of reducing cost, it would clearly be desirable to develop a process which can make use of relatively inexpensive feedstock, eg. secondary or tertiary alcohols and ketones derived from the oxidation of paraffin. It would also be desirable to provide a process whereby primary alcohols are produced using a smaller number of steps than currently known processes.

It has now surprisingly been found that by reacting secondary alcohols, primary alcohols or ketones, or mixtures of one or more of these, with carbon monoxide and hydrogen in the presence of excess acid and a Group VIII metal catalyst having a bidentate ligand, a "single-pot" process for producing primary alcohols is achieved.

The process of the present invention also has the advantage that it is possible to simultaneously or separately prepare olefins in addition to primary alcohols. Higher olefins are useful in drilling fluid applications as well as a variety of other applications.

A further advantage of the present invention is that there is a high selectivity towards linear primary alcohols, which are known to be more biodegradable than branched primary alcohols and therefore are particularly useful intermediates for surfactants which are used in laundry detergent applications.

SUMMARY OF THE INVENTION

According to one aspect of the present invention there is provided a process for producing primary alcohols from secondary or tertiary alcohols or ketones wherein the process comprises reacting a secondary alcohol, a tertiary alcohol or a ketone, or a mixture thereof, with carbon monoxide and hydrogen in the presence of a catalyst which is comprised of:

(i) a source of Group VIII metal, (ii) a bidentate ligand having the general formula (I):

$$R^1R^2M^1\text{-}R\text{-}M^2R^3R^4 \qquad (I)$$

wherein $M^1$ and $M^2$ are independently P, As or Sb;

$R^1$ and $R^2$ together represent a bivalent substituted or unsubstituted cycloaliphatic group whereby the two free valencies are linked to $M^1$; $R^3$ and $R^4$ independently represent a substituted or unsubstituted hydrocarbyl group, or together represent a bivalent substituted or unsubstituted cycloaliphatic group whereby the two free valencies are linked to $M^2$;

and R represents a bivalent organic bridging group; and (iii) an acid having a $pK_a$ of 3 or less, wherein the acid is in stoichiometric excess to the Group VIII metal.

DETAILED DESCRIPTION OF THE INVENTION

The process of the present invention is carried out in the presence of a stoichiometric excess of acid over the Group VIII metal. Suitable acids are those having a $pK_a$ of 3 or less, measured in aqueous solution at 18° C. Any acid having a $pK_a$ of 3 or less is suitable for use herein. Preferred acids have a $pK_a$ of 2.5 or less, more preferably 2 or less.

As used herein, the term $pK_a$ is the negative logarithm of the equililbrium constant $K_a$, i.e. $pK_a=-\log K_a$, wherein for any acid HA which partially dissociates in solution, the equilibrium $HA=HA^++A^-$ is defined by an equilibrium constant $K_a$, where $$K_a = \frac{[H^+][A^-]}{[HA]}$$

Examples of suitable acids include, but are not limited to, phosphoric acid, sulphuric acid, sulphonic acids, phosphonic acid, halogenated phosphonic acids such as fluorophosphonic acid, carboxylic acids, halogenated carboxylic acids such as trifluoroacetic acid, aromatic carboxylic acids, and mixtures thereof.

Sulphonic acids are in particular preferred, for example, methanesulphonic acid, trifluoromethanesulphonic acid, tert-butanesulphonic acid, p-toluenesulphonic acid and 2,4,6-trimethylbenzenesulphonic acid. An especially preferred acid for use in the process herein is a mixture of methanesulphonic acid and phosphoric acid.

The process of the present invention is carried out in the presence of a catalyst based on a Group VIII metal and a bidentate ligand of formula (I) above. In the present specification the preferred Group VIII metals are defined as the metals rhodium, nickel, palladium and platinum. Of these, palladium and platinum are preferred, especially palladium.

Examples of suitable metal sources are platinum or palladium compounds such as salts of palladium or platinum and nitric acid, sulphuric acid or sulphonic acids, salts of platinum or palladium and carboxylic acids with up to 12 carbon atoms, palladium or platinum complexes, e.g. with carbon monoxide or acetylacetonate, or palladium or platinum combined with a solid material such as an ion exchanger or carbon. Palladium(II) acetate and platinum(II) acetylacetonate are examples of preferred metal sources.

In the bidentate ligand of formula (I) above, $M^1$ and $M^2$ are preferably the same and more preferably they both represent phosphorus atoms, in which case the ligands are bisphosphines.

In the general formula (I), R represents a bivalent organic bridging group, preferably containing from 1 to 10, more preferably from 2 to 6, even more preferably from 2 to 4 and especially from 2 to 3 atoms in the bridge. A most preferred embodiment has 2 atoms in the bridge.

By "in the bridge" is understood to be the shortest connection between the atoms $M^1$ and $M^2$. The bridge can be substituted. In certain embodiments the bridge is substituted with at least two substituents. The bridge can be substituted on any part of the bridge but preferably on the carbon atom of the bridging group connected to $M^1$ and $M^2$.

Suitable bridging groups include substituted and unsubstituted alkylene groups. The alkylene groups can optionally contain one or more heteroatoms, such as N, S, Si or O. Preferably, however, the alkylene group contains only carbon atoms in the bridge, preferably 2 or 3 carbon atoms, most preferably 2 carbon atoms.

The alkylene groups can be substituted with one or more substituents, preferably at least 2 substituents. The substituents can be attached to any part of the connection. In a preferred embodiment, the carbon atoms of the connection, which are connected to the $M^1$ and $M^2$ atoms are substituted. In this case the bidentate ligand has two chiral C-atoms and can have the RR, SS or R,S meso form. The R,S-meso form is preferred.

The substituents on the alkylene bridging group can contain carbon atoms and/or heteroatoms. Suitable substituents include hydrocarbyl groups which may optionally contain heteroatoms such as Si, S, N or O, halides such as chloride, bromide, iodide, thiol, —OH, $A^1$-O—, —S-$A^1$, —CO-$A^1$, —$NH_2$, —$NHA^1$, —$NA^1A^2$, —CO—$NA^1A^2$, —$PO_4$, —$NO_2$, —NOH, —CO, —$SO_2$, —SOH in which $A^1$ and $A^2$, independently, are aliphatic groups preferably having from 1 to 10 carbon atoms, more preferably 1 to 4 carbon atoms, eg. methyl, ethyl, propyl and isopropyl.

Preferably, when the alkylene bridging group is substituted, the substituents are hydrocarbyl groups.

These may be straight-chain or branched and saturated or unsaturated. The hydrocarbyl substituents can be aromatic or aliphatic.

Suitable aromatic hydrocarbyl substituents can be aryl groups such as phenyl and $C_1$–$C_4$ alkyl phenyl groups.

Suitable aliphatic hydrocarbyl substituents are linear or branched alkyl or cycloalkyl groups, preferably having from 1 to 10 carbon atoms, more preferably 1 to 4 carbon atoms.

Preferred hydrocarbyl substituents are $C_1$–$C_4$ alkyl groups, preferably methyl, ethyl, propyl, isopropyl, butyl, isobutyl, most preferably methyl.

Preferred substituents on the alkylene bridging groups are aliphatic alkyl groups.

Examples of non-substituted alkylene bridging groups include methylene, ethylene and trimethylene groups. Examples of substituted alkylene bridging groups include 2,2-dimethyl-trimethylene, 2,2-diethyl-trimethylene, 2,2-dimethyl-tetramethylene, 2-methyl, 2-hydroxymethyl-trimethylene and 2,2-di-hydroxymethyl-trimethylene.

In particularly preferred embodiments herein the bridging group is ethylene, that is, —$CH_2$—$CH_2$—.

Other suitable bridging groups are those where the connection forms part of an aliphatic or aromatic ring structure. Such bridging groups can contain one or more substituted or unsubstituted, saturated or unsaturated aliphatic ring structures and/or one or more substituted or unsubstituted aromatic ring structures. Preferably such a bridging group still contains only 2 to 6 carbon atoms in the bridge.

Suitable aliphatic ring structures include cyclopentane, cyclohexane, cyclohexene, cyclopentene, 3,4-furan and 3,4-thiophene. The cycloaliphatic ring may be interrupted by one or more heteroatoms such as N, S, Si or O.

The ring structures may be substituted with any kind of substituent, including heteroatoms, alkyl groups, cycloalkyl groups and aryl groups. Suitable substituents include those mentioned above in relation to alkylene bridging groups. It is preferred that $M^1$ and $M^2$ are attached to the ring system at adjacent positions, i.e. positions 1 and 2.

An example of a bridging group containing aromatic rings is one which contains two aromatic rings, preferably two benzene rings. These aromatic ring structures are preferably connected to each other and to two alkylene groups, which in their turn are connected respectively to $M^1$ and $M^2$. The alkylene groups are preferably connected to the aromatic ring structures at their ortho positions with respect to the carbon atoms with which the aromatic ring structures are connected.

The bivalent bridging group can also include organometallic groups such as ferrocylene as in WO95/06027 or orthoanellated systems as in WO95/30680, connecting the atoms $M^1$ and $M^2$ through carbon atoms.

$R^1$ and $R^2$ together and/or $R^3$ and $R^4$ together can represent an optionally substituted bivalent cyclo-aliphatic group. Further $R^3$ and $R^4$ may independently be substituted or unsubstituted hydrocarbyl groups.

Suitable hydrocarbyl groups are alkyl, cycloalkyl and aryl groups preferably containing from about 1 to 10 carbon atoms. Examples of suitable hydrocarbyl groups include alkyl groups having from 1 to 6 carbon atoms such as ethyl, propyl, isopropyl, butyl, sec-butyl, iso-butyl, tert-butyl, pentyl, sec-pentyl and hexyl, cycloalkyl groups such as cyclopentyl and cyclohexyl groups, aryl groups such as phenyl and tolyl groups and bivalent groups such as a hexamethylene group.

It is preferred herein that both $R^1$ and $R^2$ together and $R^3$ and $R^4$ together represent an optionally substituted bivalent cycloaliphatic group.

By "cycloaliphatic group" is understood to be a monocyclic or a polycyclic group such as bicylic or tricyclic groups. Preferred cyclic groups are bicylic groups. The cycloaliphatic group contains at least one heteroatom, i.e. the $M^1$ and $M^2$ atom respectively, but can contain more heteroatoms. Suitable heteroatoms that can further be present in the cyclic group include P, As, Sb, O, N, S and Si. The optionally substituted cycloaliphatic group contains at least 5 ring atoms. Preferably the cyclic group contains from 6 to 20 ring atoms, more preferably from 6 to 12 ring atoms, especially 6 to 10 ring atoms.

It is advantageous that the cycloaliphatic group is a cycloalkylene group, i.e. forming with the atom $M^1$ or $M^2$ a bicyclic group. Preferably $M^1$ and $M^2$ are both phosphorus and $R^1$, $R^2$ and $M^1$ together and $R^3$, $R^4$ and $M^2$ together both represent a phosphabicycloalkyl group.

One or both of the phosphabicycloalkyl rings can be substituted with one or more suitable hydrocarbyl groups containing carbon atoms and/or heteroatoms. Suitable substituents include groups containing heteroatoms such as halides, sulphur, phosphorus, oxygen and nitrogen. Examples of such groups include chloride, bromide, iodide, thiol, and groups of the general formula —$Y^1$—OH, —$Y^1$—CO—OH, —$Y^1$—SH, —S—$Y^1$, —O—$Y^1$, —CO—$Y^1$, —$NH_2$, —$NHY^1$, —$NY^1y^2$, —CO—$NY^1Y^2$, —OH, —$PO_4$, —$NO_2$, —NOH, —CO, —$SO_2$, —S—OH, in which $Y^1$ and $Y^2$, independently, represent $C_1$—$C_{10}$ alkyl groups. If a phosphabicycloalkyl ring is substituted it is preferably substituted with a carbon containing group. Such a carbon containing group can, however, contain additional heteroatoms, such as halides, sulphur, oxygen and nitrogen or hetero-groups as described hereinbefore. Preferably, substituted phosphabicycloalkyl rings are substituted with alkyl groups, preferably having from 1 to 10 carbon atoms, more preferably from 1 to 4 carbon atoms. Linear, branched or cyclic alkyl groups can be used. Suitable alkyl groups include methyl, ethyl, propyl, iso-propyl, butyl and iso-butyl. More suitably methyl groups are used. If the phosphabicycloalkyl ring is substituted, it can be mono- or poly-substituted and is preferably di-substituted. More preferably the phosphabicycloalkyl ring in this case is substituted with two methyl groups. The phosphabicycloalkyl ring can be substituted at all carbon atoms of the ring. However, the use of rings with substituents on certain carbon atoms can be more beneficial. Suitably, phosphabicyclononyl rings are used with substituents on two carbon atoms, suitably carbon atom 1, 2, 8 and carbon atom 4, 5 or 6.

Examples of suitable bivalent cycloaliphatic groups are 1,4-cyclohexylene, 1,4-cycloheptylene, 1,3-cycloheptylene, 1,2-cyclooctylene, 1,3-cyclooctylene, 1,4-cyclooctylene, 1,5-cyclooctylene, 2-methyl-1,5-cyclo-octylene, 2,6-dimethyl-1,4-cyclooctylene and 2,6-dimethyl-1,5-cyclooctylene groups. Preferred bivalent cyclic groups are selected from 1,4-cyclo-octylene, 1,5-cyclo-octylene, and methyl (di)substituted derivatives thereof, particularly 1,4-cyclo-octylene and 1,5-cyclo-octylene.

In a highly preferred embodiment the cyclic group contains 8 ring atoms and forms a 9-phosphabicyclononyl group together with a phosphorus atom. The 9-phosphabicyclononyl group can have several isomeric structures. For the purpose of the invention the [3,3,1] and [4,2,1] isomers are preferred. $R^1$ and $R^2$ together and $R^3$ and $R^4$ together can have both the same or a different isomeric structure. Preferably both $R^1$ and $R^2$ together and $R^3$ and $R^4$ together have the [3,3,1] structure. Compositions of bidentate diphosphines having a high amount of bidentate diphosphine ligand having the [3,3,1] structure for both phosphabicyclononyl groups can be prepared as described in WO02/064250.

Examples of preferred bidentate ligands of formula (I) include
2,3-PP'bis(9-phosphabicyclo[3,3,1]nonyl)-butane,
2,3-PP'bis(9-phosphabicyclo[4,2,1]nonyl)-butane,
2,3-PP'bis(9-phosphabicyclo[3,3,1]nonyl)-but-2-ene,
2,3-PP'bis(9-phosphabicyclo[4,2,1]nonyl)-but-2-ene,
2,3-PP'bis(9-phosphabicyclo[3,3,1]nonyl)-pentane,
2,4-PP'bis(9-phosphabicyclo[3,3,1]nonyl)-pentane,
2,3-PP'bis(9-phosphabicyclo[4,2,1]nonyl)-pentane,
2,4-PP'bis(9-phosphabicyclo[4,2,1]nonyl)-pentane,
2,3-PP'bis(9-phosphabicyclo[3,3,1]nonyl)-pent-2-ene,
2,3-PP'bis(9-phosphabicyclo[4,2,1]nonyl)-pent-2-ene,
1,2-PP'bis(9-phosphabicyclo[3,3,1]nonyl)-cyclopentane,
1,2-PP'bis(9-phosphabicyclo[4,2,1]nonyl)-cyclopentane,
1,2-PP'bis(9-phosphabicyclo[3,3,1]nonyl)-cyclohexane,
1,2-PP'bis(9-phosphabicyclo[4,2,1]nonyl)-cyclohexane,
1,2-PP'bis(9-phosphabicyclo[4,2,1]nonyl)-cyclohexene,
1,2-PP'bis(9-phosphabicyclo[4,2,1]nonyl)-cyclopentene,
3,4-PP'bis(9-phosphabicyclo[4,2,1]nonyl)-furan,
3,4-PP'bis(9-phosphabicyclo[4,2,1]nonyl)-thiophene,
1,3-bis-(1,4-cyclooctylene-phosphino)-propane, i.e.
1,3-PP'bis(9-phosphabicyclo[4,2,1]nonyl)-propane;
1,3-bis-(1,5-cyclooctylene-phosphino)-propane, i.e.
1,3-PP'bis(9-phosphabicyclo[3,3,1]nonyl)-propane;
1,2-bis-(1,4-cyclooctylene-phosphino)-ethane, i.e.
1,2-PP'bis(9-phosphabicyclo[4,2,1]nonyl)-ethane;
1,2-bis-(1,5-cyclooctylene-phosphino)-ethane, i.e.
1,2-PP'bis(9-phosphabicyclo[3,3,1]nonyl)-ethane;
and mixtures thereof.

These ligands can be prepared by reacting P-cyclo-octylene hydride (phosphabicyclononane hydride) and butyllithium to generate a lithium cyclo-octylene phosphide (lithiated phosphabicyclononane). The later phosphide is reacted with an aliphatic group substituted with suitable leaving groups, preferably tosylates or cyclic sulfates, in an appropriate manner. Preferred aliphatic groups are those having a cyclic sulfate structure as a leaving group, such as cyclic substituted or non-substituted alkane diol sulfate esters, also called cyclic alkyl sulfates. For example 2,4-PP'bis(9-phosphabicyclo[3,3,1]nonyl)-pentane can be prepared by reacting phosphabicyclononane hydride and butyllithium to generate the corresponding lithium phosphide and subsequently reacting this lithium phosphide, at for example 0° C. or ambient temperature (25° C.) in tetrahydrofuran, with 2,4 pentanediol di-p-tosylate ester. 2,3-PP'bis(9-phosphabicyclo[3,3,1]nonyl)-butane can for example be prepared by reacting phosphabicyclononane hydride and butyllithium to generate the corresponding lithium phosphide and subsequently reacting this lithium phosphide with 2,3-butanediol cyclic sulfate ester (IUPAC name cyclic 2,3-butyl sulfate), in for example tetrahydrofuran at a temperature varying in the range from 0° C. to reflux temperature.

The P-cyclo-octylene hydride (phoshabicyclononane hydride) may conveniently be prepared as described by Elsner et al. (Chem. Abstr. 1978, vol. 89, 180154x).

Examples of ligands where the bridging group comprises a trimethylene group connecting $M^1$ or $M^2$ of which the middle carbon atom in the bridge has two additional bondings with a non-hydrogen atom are disclosed in copending U.S. application Ser. No. 10/287,731, filed Nov. 4, 2002, and WO 03/040065 (which are herein incorporated by referenced) and include:
2,2-dimethyl, 1,3-PP'bis(9-phosphabicyclo-[3,3,1]nonyl)-propane;
2-methyl, 2-hydroxymethyl, 1,3-PP'bis(9-phosphabicyclo[3,3,1]nonyl)-propane;

2,2-dimethyl, 1,3-PP'bis(9-phosphabicyclo-[4,2,1]nonyl)-propane;
2-methyl, 2-hydroxymethyl, 1,3-PP'bis(9-phosphabicyclo[4,2,1]nonyl)-propane;
and mixtures thereof.

Examples of bidentatediphosphine ligands having a dimethylenebiphenyl bridge are described in copending U.S. application Ser. No. 10/287,731, filed Nov. 4, 2002, and WO 03/040065 (which are herein incorporated by referenced) and include:
2,2'-bis-(1,4-cyclooctylene-phosphino-methyl)-1,1'-biphenyl;
2,2'-bis-(1,5-cyclooctylene-phosphino-methyl)-1,1'-biphenyl;
and mixtures thereof.

A special class of bivalent cycloaliphatic groups include tertiary cyclic structures. For example $R^1$ and $R^2$ and/or $R^3$ and $R^4$ can represent a bivalent radical that together with the phosphorus atom to which it is attached is an alkyl substituted 2-phosphatricyclo[3.3.1.1{3,7}]-decyl group or a derivative thereof in which one or more of the carbon atoms are replaced by heteroatoms, for example, oxygen.

Preferably the ligand comprising the alkyl substituted 2-phospha-tricyclo[3.3.1.1{3,7}]decyl group is a compound according to Formula (II), wherein $R^5$ are alkyl groups of 1-6 carbon atoms, preferably methyl.

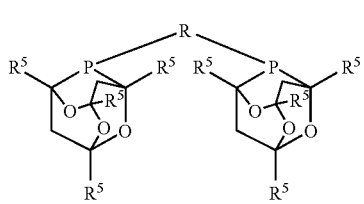

(II)

Examples of such ligands include 2,3-P,P'-di(2-phospha-1,3,5,7-tetramethyl-6,9,10-trioxatricyclo-[3.3.1.1{3.7}decyl)butane and 2,4-P,P'-di(2-phospha-1,3,5,7-tetramethyl-6,9,10-trioxatricyclo[3.3.1.1{3.7}-decyl) pentane. Such ligands can be prepared as described in more detail in WO-A-98/42717.

Another class of ligands suitable for use herein include those ligands derived from limonene and disclosed in WO02/14248.

Further details on other suitable ligands for use herein including their methods of preparation are disclosed in WO03/040065, WO02/064250, WO95/05354, WO00/56695, WO01/28972, EP-A-971940 and WO01/87899.

The most preferred ligand for use herein is 1,2-P,P'-bis (9-phosphabicyclononyl)ethane.

Conveniently, the process of the present invention may be carried out in the presence of a solvent. As such, saturated hydrocarbons, e.g. paraffins and isoalkanes are recommended and furthermore alcohols, the saturated hydrocarbons and alcohols preferably having from 4 to 10 carbon atoms per molecule, such as butanol, ethylhexanol-1, nonanol-1, or in general terms the alcohols formed as carbonylation product; ethers such as 2,5,8-trioxanonane (diglyme), diethylether and anisole, and ketones, such as methylbutylketone. Solvents, comprising or substantially consisting of sulphones are also preferred. Sulphones are in particular preferred, for example dialkylsulphones such as dimethylsulphone and diethylsulphone and cyclic sulphones, such as sulfolane (tetrahydrothiophene-2,2-dioxide), sulfolane, 2-methyl-sulfolane and 2-methyl-4-ethylsulfolane.

The quantity in which the catalyst system is used, is not critical and may vary within wide limits. Usually amounts in the range of about $10^{-8}$ to about $10^{-1}$, preferably in the range of about $10^{-7}$ to about $10^{-2}$ mole atom of Group VIII metal per mole of starting compound selected from secondary alcohol, tertiary alcohol, ketone, or mixture thereof, are used. The amounts of the participants in the catalyst system are conveniently selected such that per mole atom of platinum group metal from about 0.5 to about 10, preferably from about 1 to about 6 moles of bidentate ligand are used.

Furthermore the presence of a small amount of catalyst promoter comprising a source of halide anions, such as for example HI or HCl, can have a significant favourable effect in that the conversion reaction proceeds at high rate, even at moderate temperatures. The molar ratio between halide and platinum metal cations is preferably in the range of from about 1:20 to about 5:1.

The carbon monoxide and hydrogen may be supplied in equimolar or non-equimolar ratios, e.g. in a ratio within the range of about 5:1 to about 1:5, preferably about 3:1 to about 1:3. Preferably they are supplied in a ratio within the range of about 2:1 to about 1:2.

The process of the present invention can be suitably carried out at moderate reaction conditions. Hence temperatures in the range of about 50 to about 200° C. are recommended, preferred temperatures being in the range of about 70 to about 160° C. Reaction pressures in the range of about 5 to about 100 bar are preferred. Lower or higher pressures may be selected, but are not considered particularly advantageous. Moreover, higher pressures require special equipment provisions.

Advantageously, the reaction of secondary alcohols, and/or tertiary alcohols and/or ketones to produce primary alcohols according to the present invention can be carried out as a "single-pot" process using a single catalyst.

It is also possible to start the reaction at the paraffin stage, by first oxidising paraffin to produce a secondary alcohol, a tertiary alcohol, a ketone or mixture thereof.

Hence according to a further aspect of the present invention there is provided a process for converting paraffins to primary alcohols comprising the steps of:
(a) subjecting a paraffin feed comprising linear and/or branched paraffins to an oxidation reaction in the presence of an oxidation catalyst to form a mixture comprising secondary alcohols and/or tertiary alcohols and/or ketones; and;
(b) reacting the mixture of secondary alcohols and/or tertiary alcohols and/or ketones with carbon monoxide and hydrogen in the presence of a catalyst based on:
  (i) a source of Group VIII metal,
  (ii) a bidentate ligand having the general formula (I):

$R^1R^2M^1\text{-}R\text{-}M^2R^3R^4$ (I)

wherein $M^1, M^2, R^1, R^2, R^3, R^4$ and R are as defined hereinabove; and
  (iii) an acid having a $pK_a$ of 3 or less wherein the acid is in stoichiometric excess over the Group VIII metal.

The primary alcohols produced by the present invention will always contain one more carbon atom than the starting alcohol or ketone.

The primary alcohols produced by the present invention preferably contain from about 6 to about 18 carbon atoms, preferably from about 10 to about 16 carbon atoms. The process of the present invention has a high selectivity towards linear primary alcohol compounds as is demonstrated in the examples below.

The invention will be illustrated by the following non-limiting examples.

EXAMPLES 1–5

Examples 1–5 were carried out in a 250 ml magnetically stirred batch autoclave. The autoclave was charged with 30 ml of secondary alcohol or ketone (the type of alcohol/ketone used in each Example is shown in Table 1 below), a stoichiometric excess of acid over palladium (the type of acid and amount of acid used in each Example is shown in Table 1 below), 10 ml sulfolane, 0.25 mmol of palladium(II) acetylacetonate, 0.4 mmol of 1,2-bis(1,4-cyclooctylenephosphino)ethane and 0.1 mmol HCl. After being flushed with carbon monoxide, the autoclave was pressurized with carbon monoxide and hydrogen to a partial pressure of 20 bar and 40 bar, respectively. Subsequently, the reactor was sealed and the contents were allowed to react for 5 hours at 160° C. After cooling, a sample was taken from the contents of the reactor and analysed by Gas Liquid Chromatography. The results are given in Table 1 below. MSA is an abbreviation for methanesulphonic acid. PA is an abbreviation for phosphoric acid.

TABLE 1

| | | | Product Selectivity % | | |
|---|---|---|---|---|---|
| Eg | Acid (mmol shown in brackets) | Secondary Alcohol or ketone (30 ml) | Conversion % | Primary Alcohol (% Linearity shown in brackets) | Olefin | Ether |
| 1 | MSA (2 mmol) | 3-octanol | 20% | Nonanol 75% (72) | 10% | 10% |
| 2 | MSA (5 mmol) | 3-octanol | 76% | Nonanol 46% (75) | 40% | 14% |
| 3 | MSA (2 mmol), PA (5 mmol) | 3-octanol | 40% | Nonanol 80% (75) | 13% | 7% |
| 4 | MSA (2 mmol), PA (10 mmol) | 3-pentanol | 22% | Hexanol 86% (74) | 5% | 9% |
| 5 | MSA (2 mmol), PA (10 mmol) | 5-nonanone | 12% | Decanol 83% (78) | 6% | 4% |

Examples 1 to 5 demonstrate that the process of the present invention can be suitably used for converting secondary alcohols or ketones to primary alcohols in high yield and high selectivity for linear primary alcohols. Olefins and ethers are also formed in small amounts as byproducts.

We claim:

1. A process for converting parafins to primary alcohols comprising the steps of:
   (a) subjecting a paraffin feed comprising linear and/or branched paraffins to an oxidation reaction in the presence of an oxidation catalyst to form a mixture comprisng secondary alchols and/or tertiary alcohols and/or ketones; and;
   (b) reacting the mixture of secondary alcohols and/or tertiary alcohols and/or ketones with carbon monoxide and hydrogen in the presence of a catalyst based on:
      (i) a source of Group VIII metal,
      (ii) a bidentate ligand having the general formula (I):

$$R^1R^2M^1\text{-}R\text{-}M^2R^3R^4 \qquad (I)$$

wherein $M^1$ and $M^2$ are independently P, As or Sb; $R^1$ and $R^2$ together represent a bivalent substituted or unsubstituted cyclic aliphatic group whereby the two free valencies are linked to $M^1$; $R^3$ and $R^4$ independently represent a substituted or unsubstituted hydrocarbyl group, or together represent a bivalent or unsubstituted cyclic group whereby the two free valencies are linked to $M^2$;

and R represents a bivalent organic bridging group; and
   (iii) an acid having a $pK_a$ of 3 or less, wherein the acid is in stoichimetric excess to the Group VIII metal.

2. The process of claim 1 wherein the acid has a $pK_a$ of 2.5 or less.

3. The process of claim 2 wherein the acid has a $pK_a$ of 2 or less.

4. The process of claim 1 wherein the acid is selected from the group consisting of phosphoric acid, sulphuric acid, sulphonic acids, phosphonic acid, halogenated phosphonic acids, carboxylic acids, halogenated carboxylic acids, aromatic carboxylic acids, and mixtures thereof.

5. The process of claim 4 wherein the acid is a sulphonic acid.

6. The process of claim 5 wherein the acid is selected from the group consisting of methanesulphonic acid, trifluoromethanesulphonic acid, tert-butanesulphonic acid, p-toluenesulphonic acid and 2,4,6-trimethylbenzenesulphonic acid.

7. The process of claim 1 wherein the acid is a mixture of methane sulphonic acid and phosphoric acid.

8. The process of claim 1 wherein the Group VIII metal is selected from the group consisting of rhodium, nickel, palladium, and platinum.

9. The process of claim 8 wherein the Group VIII metal is selected from the group consisting of palladium and platinum.

10. The process of claim 9 wherein the Group VIII metal is palladium.

11. The process of claim 1 wherein both $M^1$ and $M^2$ are phosphorus atoms.

12. The process of claim 1 wherein R is an aliphatic bridging group containing from 1 to 10 carbon atoms.

13. The process of claim 12 wherein R is an aliphatic bridging group containing from 2 to 6 carbon atoms.

14. The process of claim 13 wherein R is an aliphatic bridging group containing from 2 to 4 carbon atoms.

15. The process of claim 1 wherein the bivalent cyclic aliphatic groups represented by $R^1$ and $R^2$ and/or $R^3$ and $R^4$, respectively, contain from 6 to 9 ring atoms, of which one ring atom is $M^1$ and $M^2$, respectively.

16. The process of claim 15 wherein $R^1$ and $R^2$ together and $R^3$ and $R^4$ together are each a bivalent cycloaliphatic group.

17. The process of claim 1 wherein the cycloaliphatic group contains at least 5 ring atoms.

18. The process of claim 17 wherein the cycloaliphatic group contains 6 to 20 ring atoms.

19. The process of claim 1 wherein $M^1$ and $M^2$ are both phosphorus and $R^1$, $R^2$ and $M^1$ together and $R^3$, $R^4$ and $M^2$ together both represent a phosphabicycloalkyl group.

20. The process of claim 1 wherein the bivalent cycloaliphatic group is selected from the group consisting of 1,4-cyclo-octylene, 1,5-cyclo-octylene, and mixtures thereof.

21. The process of claim 1 wherein the quantity of catalyst used is from about $10^{-8}$ to about $10^{-1}$ mole atom of Group VIII metal used per mole of the compound reacted.

22. The process of claim 21 wherein the quantity of catalyst used is from about $10^{-7}$ to about $10^{-2}$ mole atom of Group VIII metal used per mole of the compound reacted.

23. The process of claim 1 wherein from about 0.5 to about 10 moles of bidentate ligand are used per mole atom of Group VIII metal.

24. The process of claim 23 wherein from about 1 to about 6 moles of bidentate ligand are used per mole atom of Group VIII metal.

* * * * *